(12) United States Patent
Borkowski et al.

(10) Patent No.: US 6,407,207 B1
(45) Date of Patent: Jun. 18, 2002

(54) CLONED AND EXPRESSED HUMAN BRADYKININ BK-2 RECEPTOR

(75) Inventors: Joseph A. Borkowski, Montclair; John W. Hess, Westfield; Catherine D. Strader, Verona, all of NJ (US); Richard W. Ransom, New Britain, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 08/148,708

(22) Filed: Nov. 8, 1993

Related U.S. Application Data

(63) Continuation of application No. 07/860,709, filed on Mar. 30, 1992, now abandoned.

(51) Int. Cl.$^7$ .................... C07K 14/705; C12N 15/12

(52) U.S. Cl. .................. 530/350; 435/69.1; 536/23.5

(58) Field of Search .................. 435/69.1; 530/350; 536/23.5

(56) References Cited

U.S. PATENT DOCUMENTS

| | | | |
|---|---|---|---|
| 4,801,613 A | 1/1989 | Stewart et al. | 514/14 |
| 4,923,963 A | 5/1990 | Stewart et al. | 530/314 |

OTHER PUBLICATIONS

Nature 347:76–79, Sep. 6, 1990, Zhou et al. cloning and expression of human and rat $D_1$ dopamine receptors.*
PNAS 86:9762–66 Dec. 1, 1989, Grandy et. al. Cloning of the cDNA and gene for a human $D_2$ dopamine receptor.*
Adriene E. McEachern et al., Expression cloning of a rat $B_2$ bradykinin receptor, Proc. Natl. Acad. Sci., USA, vol. 88 pp. 7724–7728 (1991).
Lawrence C. Mahan et al., Accelerated Communication, Functional Expression of $B_2$ Bradykinin Receptors from Balb/c Cell mRNA in Xenopus Oocytes, Molecular Pharmacology, 37:785–789 (1990).
J. G. de Vries et al., Construction of a Physiologically Active Photoaffinity Probe Based on the Structure of Bradykinin: Labelling of Angiotensin Converting Enzyme but Not Candidate Bradykinin Receptors on NG108–15 Cells, Journal of Neurochemistry, vol. 52, No. 5, pp. 1508–1516 (1989).
Richard J. Miller, Bradykinin highlights the role of phospholipid metabolism in the control of nerve excitability TINS, vol. 10, No. 6, (1987).
Donald C. Manning et al., Bradykinin receptor–mediated chloride secretion in intestinal function, Nature, vol. 299, (1982).
Larry R. Steranka et al., Bradykinin as a pain mediator: Receptors are localized to sensory neurons, and antagonists have analgesic actions, Proc. Natl. Acad. Sci. USA vol. 85 pp. 3245–3249, (1988).

Nancy E. Owen et al., Lys–Bradykinin Stimulates Na + Influx and DNA Synthesis in Cultured Human Fibroblasts, Cell, vol. 32, 979–985, (1983).
Isabel Llona et al., Identification of Pre–and Postsynaptic Bradykinin Receptor Sites in the Vas Deferens: Evidence for Different Structural Prerequites$_1$, The Journal of Pharm. and Exper. Therapeutics, vol. 241, No. 2.
Karen M. Braas et al., Bradykinin analogues: differential agonist and antagonist activities suggesting multiple receptors, Br. J. Pharmacol., 94, 3–5, (1988).
B.R. Conklin et al., Distinct Bradykinin Receptors Mediate Stimulation of Prostaglandin Synthesis by Endothelial Cells and Fibroblasts, The Journal of Pharm. and Exper. Therapeutics, vol. 244, pp. 646–649 (1987).
Robin Plevin et al., TIPS, vol. 9, (1988).
Richard Olsen et al., An Increase in Intracellular Free $Ca^2$+ Associated with Serum–free Growth Stimulation of Swiss 3T3 Fibroblasts by Epidermal Growth Factor in the Presence of bradykinin, the Journal of Biol. Chemistry, vol. 263, No. 34, pp. 18030–18035, (1988).
Ronald M. Burch et al., Dissociation of bradykinin–induced prostaglandin formation from phosphatidylinositol turnover in Swiss 3T3 fibroblasts: Evidence for G protein regulation of phospholipase $A_2$, Proc.Proc. Natl. Acad. Sci. USA, vol. 84, pp. 6374–6378, (1987).
Teresa M. Perney et al., Two Different G–proteins Mediate Neuropeptide Y and Bradykinin–stimulated Phospholipid Breakdown in Cultured Rat Sensory Neurons, The Journal of Biol. Chem., vol. 264, No. 13, pp. 7317–7327, (1989).
Catherine D. Strader et al., Mutations that Uncoupled the Beta–Adrenergic Receptor from $G_s$ and Increase Agonist Affinity, The Journal of Biol. Chem., vol. 262, No. 34, pp. 16439–16443 (1988).
Garry Gilliland et al., Analysis of Cytokine mRNA and DNA: Detection and quantitation by competitive polymerase chain reaction, Proc. Natl. Acad. Sci., USA, vol. 87, pp. 2725–2729, (1990).
Stephen G. Farmer et al., Evidence for a Pulmonary $B_3$ Bradykinin Receptor, The American Society for Pharmacology and Exp. Therapeutics, Mol. Pharm. 36:001–008, pp. 1–8, received Dec. 5, 1988, accepted Apr. 10, 1989.
David Proud et al., Kenin Formation: Mechanisms and Role in Inflammatory Disorders, Am. Rev. Immunol., 6, pp. 49–83, (1988).

(List continued on next page.)

Primary Examiner—John Ulm
(74) Attorney, Agent, or Firm—Philippe L. Durette; Melvin Winokur

(57) ABSTRACT

The present invention is a cloned human BK-2 bradykinin receptor cloned from a human lung fibroblast cell line. A cDNA clone, also part of the instant invention, encodes a novel 364 amino acid protein (the BK-2 receptor) that has the characteristics of a seven transmembrane domain G-protein coupled receptor. The invention is used to express a BK-2 bradykinin receptor in a host mammalian cell to screen for pharmaceutical antagonists or agonists which bind to or interact with the BK-2 bradykinin receptor protein.

1 Claim, No Drawings

OTHER PUBLICATIONS

J. Golay et al., A Simple and Rapid Method to Analyze Specific mRNAs from Few Cells in a Semi-quantitative Way Using the Polymerase Chain Reaction, Technical Tips, 1:144–145 (1991).

Klaus Uberla et al., Generation of Competitor DNA Fragments for Quantitative PCR, Research, 1:136–139 (1991).

Dohlman et al., Model System for the Study of Seven-Transmembrane-segment Receptors, Annu. Rev. Biochem., 60:653–88 (1991).

Marion M. Bradford, A Rapid and Sensitive Method for the Quantitation of Microgram Quantities of Protein Utilizing the Principle of Protein-Dye Binding, Analytical Biochemistry 72, 248–254 (1976).

Grant A. McPherson, Analysis of Radioligand Binding Experiments, A Collection of Computer Programs for the IBM PC, Journal of Pharmacological Methods 14, 213–228 (1985).

J.E. Taylor et al., Bradykinin-Antagonists: Therapeutic Perspectives, Drug Development Research 16:1–11 (1989).

K. Wirth et al., Hoe 140 a new potent and long acting bradykinin-antagonist: in vivo studies, Br. J. Pharmacol., 102, 774–777, (1991).

Marilyn Kozak, The Scanning Model for Translation: An Update, The Journal of Cell Biology 108, 229–241 (1989).

Donald C. Manning et al., Two Bradykinin Binding Sites with Picomolar Affinities[1], The Journal of Pharmacology and Exp. Therapeutics, vol. 237, No. 2 pp. 504–512 (1986).

Peter J. Barnes et al., Inflammatory mediators and Asthma, Pharmacological Reviews, vol. 40, No. 1, pp. 49–84 (1988).

Alexandre Trifilieff et al., Evidence for two high-affinity bradykinin binding sites in the guinea-pig lung,European Journal of Pharmacology, Mol. Pharmacology Section 207: 129–134 (1991).

Catherine D. Strader et al., Structural basis of Beta-adrenergic receptor function,The FASEB Journal Pharm. and Biochemistry, vol. 3, May (1989).

Claus Liebmann et al., Antagonist binding reveals two heterogenous $B_2$ bradykinin receptors in rat myometrial membranes, European Journal of Pharm. 199:363–365 (1991).

Richard W. Fuller et al., Bradykinin-induced Bronchoconstriction in Humans, Mode of Action [1–3], Am. Rev. Respir. Dis.: 135:176–180 (1987).

J. Fred. Hess et al., Biochemical and Biophysical Research Communications vol. 184, No. 1, pp. 260–268 (1992).

Masu et al., "cDNA Cloning of Bovine Substance-K receptor through oocyte Expression System", Nature, vol. 329, Oct. 29, 1987; pp. 836–838.

Eggerickx et al., "Molecular Cloning, Functional Expression and Pharmacological Characterization of a Human Bradykinin B2 Receptor Gene"; Biochemical and Biophysical Res. Comm. vol. 187; No. 3, 1992 pp. 1306–1313.

Fong et al., "Molecular Basis for the Species Selectivity fo the Neurokinin–1 Receptor Antagonists CP–96,345 and RP67580" The Jour. of Biol. Chem. vol. 267, No. 36, pp. 25668–25671, 1992.

Oksenberg et al. "A Single Amino Acid Difference Confs Major Pharmacological Variation Between Human and rodent 5–HT1B Receptors", Nature, vol. 360, Nov. 12, 1992 pp. 161–163.

* cited by examiner

CLONED AND EXPRESSED HUMAN BRADYKININ BK-2 RECEPTOR

This is a continuation of application Ser. No. 07/860,709 filed Mar. 30, 1992, now abandoned.

BACKGROUND OF THE INVENTION

Bradykinin is a hormonal nonapeptide (Arg-Pro-Pro-Gly-Phe-Ser-Pro-Phe-Arg)(SEQ ID NO:1) which mediates pain, vascular permeability, inflammation, gastrointestinal function, and smooth muscle tone in vascular and other tissues. Bradykinin (BK) is one of the key mediators of the body's response to trauma and injury. BK levels are generally low until a traumatic event triggers a cascade of biochemical reactions and a rise in the concentration of BK by proteolytic generation. High molecular weight precursors, the kininogens, are found in blood and tissue. This cascade is initiated by the activation of the Hageman factor which also initiates fibrinolysis and coagulation.

Receptors for BK exist in the nervous system, epithelia, smooth muscle and fibroblasts. In each tissue type BK triggers specific responses including neurotransmitter release, muscle contraction, fluid secretion by epithelia, and the stimulation of cell growth. It can also act as a neurotransmitter.

The initial interaction for biological response occurs at a BK receptor site on a cell. Specific BK antagonists have been developed (Vavrek, *Peptides,* 6, 161–165 (1985)). Their potential use includes use as anti-nociceptive and anti-inflammatory agents. Bradykinin activates neurons and produces neurotransmitter release. It also stimulates the production of a number of bioactive intermediates including inositol triphosphate (Ins-1,4,5-$P_3$) and diacylglycerol (DAG) and arachidonic acid (AA) and its cyclooxygenase and lipooxygenase products. These substances cause cellular levels of cAMP, cGMP, and $Ca^{2+}$ to increase. BK also activates phospholipase C and $A_2$. In neurons, the most important points of action for the substances released by BK stimulation are ion channels. Miller, R. J., *Trends Neurosci.,* 10, 226–228 (1987).

Bradykinin released during tissue damage causes vasodilation, increased vascular permeability, altered gut motility and pain. Specific bradykinin receptors exist in intestinal mucosa and muscle. Bradykinin and analogues stimulate Cl secretion in the gut. Specific BK receptor binding sites occur in the mucosa and in muscle. BK has a contractile effect in muscle. Manning et al., *Nature,* 299, 256–259 (1982).

Addition of nanomolar concentrations of BK to the serosal surface of the mucosal later of the guinea pig ileum rapidly increased transepithelial potential difference (p.d.) and the short circuit current ($I_{SC}$). This suggests localization of BK receptors at the serosal surface of the villus and crypt epithelium. The increase in $I_{SC}$ is thought to be due to stimulation of anion secretion (Cl out of the cell produces a larger potential difference). Manning et al., *Nature,* 299, 256–259 (1982).

Bradykinin could open calcium channels as indicated by the inhibitory effects of $Ca^{2+}$ channel blockers. Calcium may be involved in regulating BK receptor binding. See Innis et al., *Proc. Natn. Acad. Sci.,* 2630–2634 (1981). BK also stimulates sodium intake and DNA synthesis. Owen et al., *Cell,* 32, 979–985 (1983).

Excessive kinin activity may play some role in carcinoid syndrome and in inflammatory bowel disease. Patients with ulcerative colitis have abnormally high levels of active kallikrein, the kinin-releasing enzyme and plasma and tissue levels of peptidiyl dipeptidase which degrades kinins are depressed in patients with regional enteritis. Manning et al., *Nature,* 299, 256–259 (1982).

Autoradiographic studies localize BK receptor binding sites to the substantia gelatinosa, dorsal root, and a subset of small cells in both the dorsal root and trigeminal ganglia of the guinea pig. Binding was also observed over myocardial/coronary visceral afferent fibers. The localization of BK receptors to nociceptive pathways supports a role for BK in pain mediation. Several BK antagonists block BK induced acute vascular pain in the rat. BK antagonists also relieve BK and urate induced hyperalgesia in the rat paw. These results indicate that BK is a physiologic mediator of pain and that BK antagonists have analgesic activity in both acute and chronic pain models. The BK receptor involved in vascular pain may be different from the receptor involved in cutaneous hyperalgesia. Steranka et al., *Proc. Natl. Acad. Sci. USA.,* 85, 3245–3249 (1988).

BK receptors have been classified as two major subtypes—$B_1$ and $B_2$. The BK metabolite des-Arg-bradykinin is a $B_1$ receptor agonist which has higher potency than BK but it is inactive at $B_2$ receptors. Steranka et al., *Proc. Natl. Acad. Sci. USA.,* 85, 3245–3249 (1988). BK also binds to G protein-coupled receptors that activate phospholipase C or phospholipase $A_2$ and increases synthesis of inositol triphosphate or arachidonic acid. Olsen et al., *J. Bio. Chem.* 263, 18030–18035 (1988). G-proteins are a family of membrane proteins that become activated only after binding guanosine triphosphate (GTP). Activated G-proteins in turn activate an amplifier enzyme on the inner face of a membrane; the enzyme then converts precursor molecules into second messengers. For example, an external signal molecule (bradykinin) may bind to its cell-surface receptor (BK-2) and induce a conformational change in the receptor. This change is transmitted through the cell membrane to a G-protein, making it able to bind to GTP. Binding of GTP causes another conformational change in the G-protein that enables it to activate adenylate cyclase (amplifier enzyme) to initiate formation of cAMP (second messenger).

In Swiss 3T3 fibroblasts, BK stimulated phospholipase C mediated InsP formation and PGE-2 synthesis. G proteins were implicated in the mediation of the effects of bradykinin suggesting that the receptor is bound to a G protein which interacts with the particular enzyme. Burch et al., *Proc. Natl. Aca. Sci. USA,* 84, 6374–6377 (1987). Two different G-proteins mediate neuropeptide Y and bradykinin stimulated phospholipid breakdown in cultured rat sensory neurons. Perney et al., *J Biol. Chem.,* 264, 7371–7327 (1991).

It is known that there is a large degree of heterogenicity within the muscarinic, adrenergic, and serotonergic class of receptors. Furthermore, "[s]imple classification of subtypes of BK receptors cannot fully account for the properties of these receptors on cells from a variety of tissues." Mahan et al., *Mol. Pharmacol.,* 37, 785–789 (1990).

Bradykinin induced increases in InsP formation through the activation of phosphatidylinositol-specific phospholipase C and subsequent mobilization of intracellular $Ca^{2+}$ and direct activation of phospholipase $A_2$, which causes the release of arachidonate and subsequent synthesis of prostaglandin $E_2$ have been found to exist in Swiss albino mouse 3T3 cells and BALBc (SV-T2) mouse 3T3 cells and involve receptors coupled to pertussis toxin-insensitive G proteins. These receptors belong to the $B_2$ subtype. Mahan et al., *Mol. Pharmacol.,* 37, 785–789 (1990).

The effect of bradykinin on the neuroeffector junction of the isolated rat vas deferens has been studied. Llona et al., J. Pharmacol. Exp. Ther., 241, 608–614 (1987). BK potentiated the magnitude of the muscular response to the electrically driven twitches and contracted the smooth muscle generating an increased muscle tone. The former action is referred to as the neurogenic or presynaptic effect and the latter is called the musculotropic or postjunctional action. The rat vas deferens contains bradykinin receptors on the nerve endings and on the smooth muscle membrane. The structural prerequisites for the activation of these receptor sites appear to be slightly different. Their results support the existence of $B_2$ receptors. des-$Arg^9$-BK and des-$Arg^9$-[$Leu^8$]-BK are inactive in causing either pre- or postsynaptic BK like responses and incubation of des-Arg-9-[$Leu^8$]-BK at high concentrations failed to antagonize BK responses in the vas deferens. This peptide is a known $B^1$ antagonist. The authors suggest that there are several classes of BK-2 receptors. Llona et al., J. Pharmacol. Exp. Ther., 241, 613 (1987). See also Brass et al., Br. J. Pharmacol., 94, 3–5 (1988).

As indicated, BK mediates vasodilation, pain and smooth muscle contraction in a number of tissues. Many of these biological actions may result from the release of arachidonic acid and its metabolites. The major metabolite in Swiss 3T3 cells (fibroblasts) is $PGE_2$ which induces smooth muscle contraction, mitogenesis, an increase in intracellular free calcium and stimulates adenylate cyclase (to produce cAMP). BK activates phospholipases which control intracellular arachidonate. Conklin et al., J. Pharmacol. Exp. Ther., 244, 646–649 (1988).

Phospholipases are considered to be the rate limiting enzymes in receptor mediated arachidonate release. BK activates $PLA_2$, a phospholipase which cleaves arachidonic acid directly from the parent phospholipid. In contrast, BK in CPAE cells (bovine pulmonary artery endothelial cells) stimulates activity of a phosphatidylcholine-specific PLC which provides arachidonate substrate for $PGI_2$ synthesis. The authors conclude that the BK receptors are pharmacologically distinct and that more BK subtypes exist beyond $BK_1$ and $BK_2$. Conklin et al., J. Pharmacol. Exp. Ther., 244, 646–649 (1988).

To further clarify the role of bradykinin, kinins are released in response to tissue injury and activate sensory pain fibers, contract venous smooth muscle and stimulate prostacyclin ($PGI_2$) synthesis and endothelium derived relaxing factor (EDRF). Blood flow to the damaged area and vascular permeability increase to cause inflammation. Plevin et al., Trends Pharmacol. Sci., 9, 387–389 (1988). Multiple $B_2$ BK receptors in mammalian tissues are present. The tissues include guinea-pig ileum, vas deferens prejunctional, N1E-115 P1 response (neuronal cell line), Rat uterus, and guinea-pig trachea (endothelial cells-BK linked to second messenger and coupled to a G-protein).

Because of the potential molecular heterogenicity of bradykinin receptors in cells and discrepancies in their pharmacological classification, there is a need to elucidate and fully characterize a homogeneous human bradykinin receptor and to express this receptor to measure antagonist or agonist response or interaction.

It is known that cDNAs for a number of receptors of the G protein-coupled superfamily have been cloned. These include, for example, a beta-adrenergic receptor, a substance P receptor, and a neurotensin receptor. Strader et al., Nature 321, 75–79 (1986); Yokata et al., J. Biol. Chem. 264, 17649–17652 (1989); Tanaka et al., Neuron 4, 847–854 (1990).

SUMMARY OF THE INVENTION

The present invention is a cloned human BK-2 bradykinin receptor cloned from a human lung fibroblast cell line. A cDNA clone, also part of the instant invention, encodes a novel 364 amino acid protein (BK-2 receptor) that has the characteristics of a seven transmembrane domain G-protein coupled receptor. The present invention is directed to a protein having an activity equal to that of human bradykinin BK-2 receptor wherein this protein is free of other human receptor proteins or substantially free of other human receptor proteins.

This invention claims a human bradykinin BK-2 receptor protein which is free of other human proteins and is a recombinantly produced receptor derived from human cells. This invention claims a human bradykinin receptor protein comprising 364 amino acids with the particular amino acid sequence of (SEQ ID NO: 2).

This invention also is directed to a pharmaceutical composition for inhibiting the binding of bradykinin to human bradykinin BK-2 receptor wherein the composition comprises an effective amount of bradykinin BK-2 receptor. It is further directed to a method of inhibiting the binding of bradykinin to human bradykinin BK-2 receptor, in a patient in need of such inhibition, comprising administration of an effective amount of bradykinin BK-2 receptor.

This invention is also directed to a DNA sequence encoding human bradykinin BK-2 receptor wherein the sequence is free of other human DNA sequences. This invention claims an open reading frame coding for the human BK-2 bradykinin receptor protein with the DNA sequence (SEQ ID NO:3) or a degenerate variation thereof. This invention further claims a DNA sequence comprising the sequence (SEQ ID NO:4) or a degenerate variation thereof. This invention further comprises a DNA sequence (SEQ ID NO:5) or a degenerate variation thereof.

This invention comprises a DNA sequence which is SEQ ID NO: 6 or a degenerate variation thereof. This invention is directed to a DNA sequence which is (SEQ ID NO:4) or a degenerate variation thereof.

Also claimed is an oligonucleotide probe that is capable of hybridizing with DNA that encodes the bradykinin BK-2 receptor and which is labeled with a detectable moiety. The oligonucleotide probe is of the sequence (SEQ ID NO: 7) or a degenerate variation thereof.

This invention is directed to an expression construct, which comprises a mammalian cell vector, and the base sequence encoding human bradykinin BK-2 receptor protein. This expression construct may be pCDNAI-Neo, and the base sequence encoding human bradykinin BK-2 receptor protein. The expression construct contains a DNA sequence which comprises the sequence (SEQ ID NO: 3) or a degenerate variation thereof. The expression construct further comprises the sequence which is (SEQ ID NO: 4) or a degenerate variation thereof. The expression construct further comprises the sequence which is (SEQ ID NO: 5) or a degenerate variation thereof.

This invention claims COS cells or Chinese Hamster Ovarian (CHO) cells transfected with an expression construct as defined above. Other mammalian cells or cell lines may also be treated with an expression construct including plasmids which contain a recombinant DNA sequence that codes for the human BK-2 bradykinin receptor protein. The expression construct or the transfected cell line may contain the necessary promoter sequence and the transcriptional and translational proteins or biomolecules necessary to express the human bradykinin receptor protein in the selected cell line.

This invention also claims a method of using a COS-7 cell line, said line transfected with an expression construct wherein the expression construct comprises a mammalian expression vector, and the base sequence encoding human bradykinin BK-2 receptor protein, comprising the steps of: expressing cloned human bradykinin BK-2 receptor in the COS-7 cells; incubating radiolabeled bradykinin and an optional test compound with the expressed human bradykinin BK-2 receptor to form a radiolabeled bradykinin-receptor complex or a test compound-receptor complex; separating said radiolabeled-receptor complex or said test compound-receptor complex from unbound radiolabeled bradykinin; measuring the amount of said radiolabeled-receptor complex. A mammalian expression vector used in the present invention is pcDNA I-Neo.

This invention is also directed to a CHO cell line wherein the cell line is transfected with an expression construct containing the cloned human BK-2 bradykinin receptor gene. It is also directed to a method of using a Chinese hamster ovarian cell line wherein the cell line is transfected with an expression construct and the expression construct comprises a mammalian expression vector, and the base sequence encoding human bradykinin BK-2 receptor protein, comprising the steps of: expressing cloned human bradykinin BK-2 receptor in the Chinese hamster ovarian cells; incubating radiolabeled bradykinin and an optional test compound with the expressed human bradykinin BK-2 receptor to form a radiolabeled bradykinin-receptor complex or a test compound-receptor complex; separating the radiolabeled-receptor complex or the test compound-receptor complex from unbound radiolabeled bradykinin; and measuring the amount of the radiolabeled-receptor complex. The mammalian expression vector used in the above method is pcDNA I-Neo.

This invention also claims a method of using a Chinese hamster ovarian cell line, said line transfected with an expression construct wherein the expression construct comprises a mammalian expression vector, and the base sequence encoding human bradykinin BK-2 receptor protein, comprising the steps of: expressing cloned human bradykinin BK-2 receptor in the Chinese hamster ovarian cells; equilibrating the expressed human bradykinin receptor with fura-2 to incorporate the fura-2 into the Chinese hamster ovarian cell; washing the Chinese hamster ovarian cell to remove unassociated fura-2; incubating the washed Chinese hamster ovarian cell with bradykinin and an optional test compound to induce an intracellular $Ca^{2+}$ release; photometrically measuring the intracellular $Ca^{2+}$ release. The mammalian expression vector used in the above method is pcDNA INeo.

DETAILED DESCRIPTION

The present invention is a cloned human BK-2 bradykinin receptor protein and DNA sequence that codes for this protein receptor. It is known that a rat BK-2 bradykinin receptor has been cloned and expressed in *Xenopus laevis* oocytes. See McEachern et al., Proc. Natl. Acad. Sci. USA 88, 7724–7728 (1991). In this reference, the authors describe the isolation of a cDNA encoding a functional smooth muscle bradykinin BK-2 receptor from a rat uterus library by a clonal selection strategy. This cDNA was expressed in *Xenopus laevis* oocytes and assayed for bradykinin responses. The predicted protein is homologous to the seven transmembrane G protein-coupled superfamily of receptors.

The present invention, however, is directed to the isolation and characterization of a cloned human BK-2 bradykinin receptor protein and is therefore critical for assisting in the discovery of therapeutic compounds that act as antagonists or as an agonist of the human BK-2 receptors.

This invention describes the cloning and expression of a human bradykinin BK-2 receptor and is therefore critical for drug antagonist or agonist studies and for eventual treatment of disorders or diseases associated with bradykinin elicited responses. Previously, rat or guinea pig tissues were utilized to screen for BK antagonists. The cloned human BK receptor circumvents the problem of species variability and therefore is valuable for human agonist or antagonist studies. The cloned DNA claimed in the instant invention provides a significant advantage over human cell lines containing the BK receptor in antagonist or agonist studies because of the potential problem of various receptor subtypes in a given cell line. Expression of the human BK-2 receptor in a cell line lacking any endogenous BK receptors alleviates this problem. Advantageously, expression of the cloned human BK-2 receptor in a cell line that lacks endogenous BK receptors permits the identification of compounds that specifically interact with this receptor. In a preferred embodiment, the cloned human BK-2 receptor will be introduced into a stable mammalian expression system which will be used to screen for antagonists of the BK-2 receptor.

This invention concerns a human bradykinin BK-2 receptor protein. (SEQ. ID NO: 2).

```
Met Leu Asn Val Thr Leu Gln Gly Pro Thr Leu Asn Gly Thr Phe Ala
1               5                   10                  15

Gln Ser Lys Cys Pro Gln Val Glu Trp Leu Gly Trp Leu Asn Thr Ile
            20                  25                  30

Gln Pro Pro Phe Leu Trp Val Leu Phe Val Leu Ala Thr Leu Glu Asn
            35                  40                  45

Ile Phe Val Leu Ser Val Phe Cys Leu His Lys Ser Ser Cys Thr Val
        50                  55                  60

Ala Glu Ile Tyr Leu Gly Asn Leu Ala Ala Ala Asp Leu Ile Leu Ala
65                  70                  75                  80

Cys Gly Leu Pro Phe Trp Ala Ile Thr Ile Ser Asn Asn Phe Asp Trp
                85                  90                  95

Leu Phe Gly Glu Thr Leu Cys Arg Val Val Asn Ala Ile Ile Ser Met
                100                 105                 110
```

```
                            -continued
Asn Leu Tyr Ser Ser Ile Cys Phe Leu Met Leu Val Ser Ile Asp Arg
        115                 120                 125

Tyr Leu Ala Leu Val Lys Thr Met Ser Met Gly Arg Met Arg Gly Val
        130                 135                 140

Arg Trp Ala Lys Leu Tyr Ser Leu Val Ile Trp Gly Cys Thr Leu Leu
145                     150                 155                 160

Leu Ser Ser Pro Met Leu Val Phe Arg Thr Met Lys Glu Tyr Ser Asp
                165                 170                 175

Glu Gly His Asn Val Thr Ala Cys Val Ile Ser Tyr Pro Ser Leu Ile
            180                 185                 190

Trp Glu Val Phe Thr Asn Met Leu Leu Asn Val Val Gly Phe Leu Leu
        195                 200                 205

Pro Leu Ser Val Ile Thr Phe Cys Thr Met Gln Ile Met Gln Val Leu
        210                 215                 220

Arg Asn Asn Glu Met Gln Lys Phe Lys Glu Ile Gln Thr Glu Arg Arg
225                 230                 235                 240

Ala Thr Val Leu Val Leu Val Val Leu Leu Leu Phe Ile Ile Cys Trp
                245                 250                 255

Leu Pro Phe Gln Ile Ser Thr Phe Leu Asp Thr Leu His Arg Leu Gly
                260                 265                 270

Ile Leu Ser Ser Cys Gln Asp Glu Arg Ile Ile Asp Val Ile Thr Gln
        275                 280                 285

Ile Ala Ser Phe Met Ala Tyr Ser Asn Ser Cys Leu Asn Pro Leu Val
        290                 295                 300

Tyr Val Ile Val Gly Lys Arg Phe Arg Lys Lys Ser Trp Glu Val Tyr
305                 310                 315                 320

Gln Gly Val Cys Gln Lys Gly Gly Cys Arg Ser Glu Pro Ile Gln Met
                325                 330                 335

Glu Asn Ser Met Gly Thr Leu Arg Thr Ser Ile Ser Val Glu Arg Gln
            340                 345                 350

Ile His Lys Leu Gln Asp Trp Ala Gly Ser Arg Gln
        355                 360
```

This receptor protein comprises a 364 amino acid sequence wherein the protein is substantially free of other human receptor proteins. This invention also encompasses mutated proteins which have substantially similar binding activities to the cloned and expressed protein claimed in this invention.

A pharmaceutical composition containing human bradykinin receptor may be used to inhibit the binding of bradykinin to cellular bradykinin BK-2 receptor wherein the composition contains an effective amount of bradykinin BK-2 receptor. This invention further concerns a method of inhibiting the binding of bradykinin to cellular human bradykinin receptor, in a patient in need of such inhibition comprising administration of an effective amount of human BK-2 receptor.

This invention is also directed to a DNA sequence encoding human bradykinin BK-2 receptor complementary DNA wherein this DNA is free of other human DNA sequences: (SEQ. ID NO: 6).

```
CTCCGAGGAG GGGTGGGGAC GGTCCTGACG GTGGGGACAT CAGGCTGCCC CGCAGTACCA    60
GGGAGCGACT TGAAGTGCCC ATGCCGCTTG CTCCGGGAGA AGCCCAGGTG TGGCCTCACT   120
CACATCCCAC TCTGAGTCCA AATGTTCTCT CCCTGGAAGA TATCAATGTT TCTGTCTGTT   180
CGTGAGGACT CCGTGCCCAC CACGGCCTCT TTCAGCGCCG ACATGCTCAA TGTCACCTTG   240
CAAGGGCCCA CTCTTAACGG GACCTTTGCC CAGAGCAAAT GCCCCAAGT  GGAGTGGCTG   300
GGCTGGCTCA ACACCATCCA GCCCCCCTTC CTCTGGGTGC TGTTCGTGCT GGCCACCCTA   360
GAGAACATCT TTGTCCTCAG CGTCTTCTGC CTGCACAAGA GCAGCTGCAC GGTGGCAGAG   420
ATCTACCTGG GGAACCTGGC CGCAGCAGAC CTGATCCTGG CCTGCGGGCT GCCCTTCTGG   480
```

-continued

```
GCCATCACCA TCTCCAACAA CTTCGACTGG CTCTTTGGGG AGACGCTCTG CCGCGTGGTG    540

AATGCCATTA TCTCCATGAA CCTGTACAGC AGCATCTGTT TCCTGATGCT GGTGAGCATC    600

GACCGCTACC TGGCCCTGGT GAAAACCATG TCCATGGGCC GGATGCGCGG CGTGCGCTGG    660

GCCAAGCTCT ACAGCTTGGT GATCTGGGGG TGTACGCTGC TCCTGAGCTC ACCCATGCTG    720

GTGTTCCGGA CCATGAAGGA GTACAGCGAT GAGGGCCACA ACGTCACCGC TTGTGTCATC    780

AGCTACCCAT CCCTCATCTG GGAAGTGTTC ACCAACATGC TCCTGAATGT CGTGGGCTTC    840

CTGCTGCCCC TGAGTGTCAT CACCTTCTGC ACGATGCAGA TCATGCAGGT GCTGCGGAAC    900

AACGAGATGC AGAAGTTCAA GGAGATCCAG ACGGAGAGGA GGGCCACGGT GCTAGTCCTG    960

GTTGTGCTGC TGCTATTCAT CATCTGCTGG CTGCCCTTCC AGATCAGCAC CTTCCTGGAT   1020

ACGCTGCATC GCCTCGGCAT CCTCTCCAGC TGCCAGGACG AGCGCATCAT CGATGTAATC   1080

ACACAGATCG CCTCCTTCAT GGCCTACAGC AACAGCTGCC TCAACCCACT GGTGTACGTG   1140

ATCGTGCGCA AGCGCTTCCG AAAGAAGTCT TGGGAGGTGT ACCAGGGAGT GTGCCAGAAA   1200

GGGGGCTGCA GGTCAGAACC CATTCAGATG GAGAACTCCA TGGGCACACT GCGGACCTCC   1260

ATCTCCGTGG AACGCCAGAT TCACAAACTG CAGGACTGGG CAGGGAGCAG ACAGTGAGCA   1320

AACGCCAGCA GGGCTGCTGT GAATTTGTGT AAGGATTGAG GGACAGTTGC TTTTCAGG    1378
```

It is also well known, that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

This invention is directed to a complementary DNA sequence encoding a full length BK-2 receptor beginning with a codon at nucleotide 136 and ending at the in-frame translation termination codon 1315 (SEQ ID NO: 3) This invention is further directed to a partial cDNA derived from human uterus of 386 nucleotides which encompasses nucleotides 540 to 926 of the gene for the full length BK-2 receptor and is used as a probe to screen a cDNA library prepared from a human fibroblastic lung cell line (SEQ ID NO: 7). In addition, this invention describes and claims two positive clones CCD-16-2 (0.78 kb) (SEQ ID NO: 8) and CCD-16-6 (1.1 kb) (SEQ ID NO: 9).

This invention also concerns and claims systems for expressing a human bradykinin BK-2 receptor. This system includes mammalian expression vectors which incorporate a base sequence encoding human bradykinin BK-2 receptor protein. This expression vector is then used to transfect a suitable expression host which translates the genetic information, synthesizes the protein or partial protein, and enables expression of the cloned BK-2 receptor protein.

This invention further claims a method of using an expression system containing a cloned human bradykinin BK-2 receptor to determine the binding affinity of bradykinin, bradykinin receptor antagonists, a bradykinin receptor agonist, or bradykinin analogues. A suitable vector containing a cDNA of human bradykinin BK-2 receptor is prepared according to the methods described in the instant invention, transfected into an appropriate host system, such as COS-7 or CHO, expressing a BK-2 bradykinin receptor protein, and contacting the described system with labeled bradykinin. After a period of incubation, the cellular mixture is filtered to separate bound material from unbound material with the radiolabeled and bound material (receptor plus bradykinin) quantified by liquid scintillation counting or other suitable means. This method further comprises competitive binding assays using bradykinin receptor antagonists, agonists, and analogues. This method comprises the steps of:

(1) expressing human BK-2 receptor in a suitable expression host such as COS-7 or CHO;

(2) treating the human BK-2 receptor with radiolabeled bradykinin while simaltaneously treating the human BK-2 receptor with a test compound to form a receptor-ligand complex;

(3) separating radiolabeled receptor-ligand complex from unbound radiolabeled bradykinin;

(4) measuring the radioactivity of bound radiolabeled bradykinin.

Alternatively, other suitable binding assays may be used to detect and moniter the activity of an expressed bradykinin receptor. For example, in CHO cells the release of intracellular calcium stores in response to the binding of bradykinin to the expressed bradykinin BK-2 receptor may be monitered by voltage means or by chemical dye means.

A human BK-2 bradykinin receptor is cloned from the lung fibroblast cell line CCD-16Lu. The cDNA clone (SEQ ID NO: 6) encodes a 364 amino acid protein (SEQ ID NO: 2) that has the characteristics of a seven transmembrane domain G-protein coupled receptor. The predicted amino acid sequence of the human BK-2 receptor is approximately twenty percent different than the protein isolated from the smooth muscle rat BK-2 receptor (81% homologous). McEachern et al., Proc. Natl. Acad. Sci. USA 88, 7726 (1991). Transfection of the human BK-2 receptor cDNA into COS-7 cells results in the expression of high levels of specific BK binding sites. Saturation binding analysis indicates that the human BK-2 receptor expressed in COS-7 cells binds BK with a $K_D$ of 0.13 nM. Pharmacological characterization of the expressed BK receptor cells demonstrates and is consistent with a cDNA encoding for a BK-2 receptor subtype.

The particular cDNA claimed and disclosed in the instant invention is prepared, isolated, and expressed by combining reverse PCR techniques (to generate a probe) with screening methods to detect the cDNA which codes for a functional BK-2 receptor. Reverse PCR with *Thermus thermophilus* DNA polymerase (PERKIN ELMER CETUS, Norwalk Conn.) is performed using human uterine mRNA (CLONETECH, Palo Alto, Calif.). Annealing of the reverse primer and reverse transcription is done by incubating the PCR reaction minus the forward primer for 10 minutes each at room temperature, 42° C., and 60° C. Two rounds of PCR are performed using degenerate primers with the restriction site adapters, NotI on the forward primer CGGCGGC-CGCGCNAAYAAYTTYGAYTGG (SEQ ID NO: 10) and XhoI on the reverse primer CGCTCGAGCGYTTYTTYT-TYTCNGTYTG (SEQ ID NO: 11). The degenerate primers are designed using the hypothesized rat amino acid sequence of the rat BK-2 bradykinin receptor. These primers are removed using a CENTROCON 30 (AMICON, Beverly, Mass.) and a third round of PCR is performed using a second pair of nested primers (with restriction site adapters) GCGCGGCCGCAAYACNATGATHTA (SEQ ID NO: 12) and CGCTCGAGACYTCYTTRAAYTTYTTCAT (SEQ ID NO: 13). PCR products are then analyzed on a 3.5% NUSIEVE (FMC BIOPRODUCTS, Rockland, Me.) gel. A 386 bp PCR product is then subcloned into pBLUESCRIPT (STRATGENE, La Jolla, Calif.) and characterized by DNA sequence analysis. This PCR product is then used as the model for the labeled probe necessary to screen a cDNA library to detect a cDNA that codes for a BK-2 bradykinin receptor. Use of PCR to generate probes specific for uncloned genes is known. See Sambrook et al., Molecular Cloning, Volume 2, 14.7, Cold Spring Harbor Lab. Press (1989). In general, mRNA (or fragments thereof) is extracted from cells which contain the target protein and is used as a template for construction of cDNA using reverse transcriptase. This cDNA is then used as a template for degenerate pools of oligonucleotide primers and for the resultant PCR amplification products. These products are cloned into an appropriate vector, sequenced, and then used as a probe to screen a cDNA library.

Isolation of cDNA coding for the human BK-2 bradykinin receptor is accomplished by first, isolating mRNA from the human cell line CCD-16Lu (CCL 204 obtained from the ATCC, Rockville, Md.) using the INVITROGEN FAST TRACK system (Invitrogen, San Diego, Calif.) according to the manufacturer's instructions. cDNA is then prepared from mRNA using the BRL cDNA Synthesis System (BRL, Gaithersburg, Md.). See Gubler et al., Gene 25, 263 (1983) as modified by BRL. BstXI adapters are then added and the modified cDNA ligated into pcDNA II (INVITROGEN). Bacterial colonies are then plated at a density of 30,000 colonies per plate and transferred to duplicate Durulose-UV (STRATAGENE) filters using standard techniques (MANIATIS). The probe utilized for screening is generated by random primed synthesis (Boehringer Mannheim Biochemicals, Indianapolis, Ind.) of the 386 bp PCR product described above in the presence of [alpha-$^{32}$P]dCTP (NEN, Boston, Mass.). Duplicate filters are also hybridized with $1.5 \times 10^6$ cpm/ml [$^{32}$P] labeled probe in 50% formamide hybridization solution, [5×SSC, 5×Denhart's, 100 ug/ml DNA, (SIGMA, St Louis, Mo.)] at 50° C. for 12 hours. The filters are washed at high stringency in a final wash of 0.1×SSC, 0.1% SDS at 60° C. Positive colonies are then rescreened as before. Plasmid is then isolated from second round positives and the DNA sequence is determined by double strand DNA sequencing using the SANGER METHOD and SEQUENASE (US BIOCHEMICALS, Cleveland, Ohio).

In order to enable expression of the cDNA that encodes for the BK-2 bradykinin receptor, COS-7 cells are transfected using LIPOFECTIN (BRL, Gaithersburg, Md.) with 50 ug/$10^7$ cells of the BK-2 receptor cDNA subcloned into the eucaryotic expression vector pcDNA I-Neo (Invitrogen). Cells are then harvested after 72 hours and the membranes containing the expressed receptor protein are prepared by scraping the cells in phosphate buffered saline solution and centrifuging for ten minutes at 500×g. The cell pellet is then resuspended and homogenized with a Polytron in 20 mM N-tris(hydroxymethyl)methyl-2-aminoethane sulfonic acid (TES, pH 6.8 at room temperature) buffer containing 1 mM 1,10 phenanthroline. The homogenate is then centrifuged for ten minutes at 500×g. The final membrane pellet is resuspended in assay buffer (TES plus 0.1% protease free bovine serum albumin, 5 uM MK-422 (enalaprilat; Gross et al., J. Pharmacol. and Exper. Ther. 216, 552–557 (1981)) and 140 ug/ml bacitracin using a motor-driven teflon-glass tissue homogenizer. Protein determination are performed by the method of Bradford using bovine IgG as the standard. See Bradford, M. A. Anal. Biochem. 72, 248–254 (1976).

Binding assays are then performed to determine receptor antagonist or agonist interaction. The assays utilized in the instant invention follow the method of Manning et al., *J. Pharmacol. Exp. Ther.*, 237, 504–512 (1986). [$^3$H]BK at various concentrations is incubated for 60 minutes at 25° C. with approximately 50 ug membrane protein in a volume of 1 ml. The assay is terminated by filtration over Whatman GF/B filters presoaked for 3 hours in 0.1% polyethyleneimine using a BRANDEL M-24 CELL HARVESTER (BRANDEL, Gaithersburg, Md.). The tubes are then rinsed two times with 4 ml ice-cold 10 uM TES and the filter bound radioactivity is quantitated by liquid scintillation counting. Nonspecific binding is determined by performing incubation in the presence of 1 uM BK and generally represents less than 5% of the total binding at 100 pM [$^3$H]BK. Competition binding experiments, in the presence of 100 pM[$^3$H]BK, are performed with varying concentrations of the test compound (s). The competition and saturation experiments are analyzed using the EBDA program of McPherson. See McPherson, G. A. *J Pharmacol. Methods* 14, 213–218 (1985).

As indicated above, the present invention is directed to a novel human bradykinin receptor and cDNA clone encoding this receptor. This cDNA clone is isolated by a combined approach using PCR technology to generate a suitable probe that is then used to screen a cDNA library. Reverse PCR from human uterus mRNA using degenerate primers based on the amino acid sequence of the rat BK-2 receptor (McEachern et al.) is first used to obtain a 386 nucleotide partial cDNA for a human BK-2 receptor. This partial cDNA sequence (SEQ ID NO: 7) encompasses nucleotides 540 to 926 and is 87% identical to the corresponding region of the rat BK-2 cDNA (nucleotides 703 to 1089) (Data Not Shown). The 386 nucleotide partial cDNA is then used to screen, by nucleic acid hybridization, a cDNA library prepared from CCD-16Lu cells. CCD-16Lu is a human fibroblast lung cell line that contains 20,000–30,000 BK receptors per cell and is therefore particularly useful for obtaining the necessary mRNA. Two positive clones, CCD-16-2 (0.78 kb) and CCD-16-6 (1.1 kb) may be isolated from the CCD-16Lu library and subsequently characterized by DNA sequence analysis.

The DNA sequence of clone CCD-16-2 indicates that this clone beings in the 5' untranslated region of the BK-2 receptor cDNA and ends in the middle of the coding sequence (SEQ. ID NO: 8).

derived from human uterine mRNA. These results indicate that these clones are derived from the same mRNA transcription unit and this transcript is also present in human uterus.

A unique restriction site (SacI or GAGCT!C) in the overlap region of CCD-16-2 and CCD-16-6 permitted the construction of a cDNA clone encoding a full length BK-2 receptor from the cleavage fragments of the two clones

```
CCTCCGAGGA GGGGTGGGGA CGGTCCTGAC GGTGGGGACA TCAGGCTGCC CCGCAGTACC    60
AGGGAGCGAC TTGAAGTGCC CATGCCGCTT GCTCCGGGAG AAGCCCAGGT GTGGCCTCAC   120
TCACATCCCA CTCTGAGTCC AAATGTTCTC TCCCTGGAAC ATATCAATGT TTCTGTCTGT   180
TCGTGAGGAC TCCGTGCCCA CCACGGCCTC TTTCAGCGCC GACATGCTCA ATGTCACCTT   240
GCAAGGGCCC ACTCTTAACG GGACCTTTGC CCAGAGCAAA TGCCCCCAAG TGGAGTGGCT   300
GGGCTGGCTC AACACCATCC AGCCCCCCTT CCTCTGGGTG CTGTTCGTGC TGGCCACCCT   360
AGAGAACATC TTTGTCCTCA GCGTCTTCTG CCTGCACAAG AGCAGCTGCA CGCTGGCAGA   420
GATCTACCTG GGGAACCTGG CCGCAGCAGA CCTGATCCTG GCCTGCGGGC TGCCCTTCTG   480
GGCCATCACC ATCTCCAACA ACTTCGACTG GCTCTTTGGG GAGACGCTCT GCCGCGTGGT   540
GAATGCCATT ATCTCCATGA ACCTGTACAG CAGCATCTGT TTCCTGATGC TGGTGAGCAT   600
CGACCGCTAC CTGGCCCTGG TGAAAACCAT GTCCATGGGC CGGATGCGCG GCGTGCGCTG   660
GGCCAAGCTC TACAGCTTGG TGATCTGGGG GTGTACGCTG CTCCTGAGCT CACCCATGCT   720
GGTGTTCCGG ACCATGAAGG AGTACAGCGA TGAGGGCCAC AACGTCACCG CTTGT        775
```

The second clone, CCD-16-6, begins in the coding region and contains an in-frame translation termination codon (SEQ. ID NO: 9)

(SEQ ID NO: 6). The human BK-2 receptor cDNA clone contains an open reading frame from nucleotide 136-1314 (SEQ ID NO: 3). The initiator methionine codon is believed

```
TGCCCTTCTG GGCCATCACC ATCTCCAACA ACTTCGACTG GCTCTTTGGG GAGACGCTCT    60
GCCGCGTGGT GAATGCCATT ATCTCCATGA ACCTGTACAG CAGCATCTGT TTCCTGATGC   120
TGGTGAGCAT CGACCGCTAC CTGGCCCTGG TGAAAACCAT GTCCATGGGC CGGATGCGCG   180
GCGTGCGCTG GGCCAAGCTC TACAGCTTGG TGATCTGGGG GTGTACGCTG CTCCTGAGCT   240
CACCCATGCT GGTGTTCCGG ACCATGAAGG AGTACAGCGA TGAGGGCCAC AACGTCACCG   300
CTTGTGTCAT CAGCTACCCA TCCCTCATCT GGGAAGTGTT CACCAACATG CTCCTGAATG   360
TCGTGGGCTT CCTGCTGCCC CTGAGTGTCA TCACCTTCTG CACGATGCAG ATCATGCAGG   420
TGCTGCGGAA CAACGAGATG CAGAAGTTCA AGGAGATCCA GACGGAGAGG AGGGCCACGG   480
TGCTAGTCCT GGTTGTGCTG CTGCTATTCA TCATCTGCTG GCTGCCCTTC CAGATCAGCA   540
CCTTCCTGGA TACGCTGCAT CGCCTCGGCA TCCTCTCCAG CTGCCAGGAC GAGCGCATCA   600
TCGATGTAAT CACACAGATC GCCTCCTTCA TGGCCTACAG CAACAGCTGC CTCAACCCAC   660
TGGTGTACGT GATCGTGGGC AAGCGCTTCC GAAAGAAGTC TTGGGAGGTG TACCAGGGAG   720
TGTGCCAGAA AGGGGGCTGC AGGTCAGAAC CCATTCAGAT GGAGAACTCC ATGGGCACAC   780
TGCGGACCTC CATCTCCGTG GAACGCCAGA TTCACAAACT GCAGGACTGG CAGGGAGCA   840
GACAGTGAGC AAACGCCAGC AGGGCTGCTG TGAATTTGTG TAAGGATTGA GGGACAGTTG   900
CTTTTCAGG                                                           909
```

These two clones overlap for 312 nucleotides and are 100% identical in the overlap region. In addition, both clones are 100% identical in the region spanned by the probe to be at position 223 Seq. ID No., which is analogous to the proposed initiator methionine in the rat BK-2 cDNA (McEachern et al.). Although two in-frame methionine codons, at nucleotides 142 and 166, occur upstream of the proposed initiator methionine, only the methionine codon at nucleotide 223 contains the elements described by Kozak that are required for efficient initiation of translation. See Kozak, M. *J. Cell Biol.*, 108, 229–241 (1989). The in-frame translation termination codon at nucleotide 1315 is in the analogous position to the termination codon in the rat BK-2 receptor cDNA. The predicted size of the human BK-2 receptor is 364 amino acids corresponding to a weight of 41,140 Daltons.

The human BK-2 bradykinin receptor claimed in the instant invention has an overall amino acid similarity to the rat BK-2 receptor of 87% but also contains striking differences. One significant distinction between the human and rat BK-2 receptor proteins occurs in the N-terminal extracellular region of the respective proteins. The claimed human receptor has two amino acids deleted from the N-terminal extracellular region of the protein receptor while the rat BK-2 receptor retains the two amino acids. This distinction may be critical in determining and distinguishing binding characteristics of bradykinin and various antagonists or agonists to the human, versus the rat, receptor. The three potential sites of N-glycosylation seen in the rat BK-2 receptor (2 in the N-terminal domain and one in the putative extracellular loop between transmembrane helices 4 and 5) are all conserved in the human receptor. The human BK-2 receptor contains several consensus sites for phosphorylation by cAMP dependent protein kinase and protein kinase C in the third intracellular loop and in the carboxy terminal tail. In the beta-adrenergic receptor these regions appear to be involved in receptor coupling to G-proteins, and phosphorylation at analogous sites occurs during receptor desensitization. See Strader et al., FASEF 3, 1825–1832 (1989) and Dohlman, et al., Ann. Rev. Biochem. 60, 653–688. Phosphorylation of these intracellular Ser and Thr residues may affect the ability of the BK receptor to communicate with G-proteins. The highest degree of overall identity seen between the claimed human BK-2 receptor and known other proteins is with the rat angiotensin receptor (32%).

Functional expression of the human BK-2 receptor is obtained by placing the entire BK-2 clone under the control of the CMV promoter (Human cytomeyalo virus) in the eucaryotic expression vector, pCDNAI-Neo (Invitrogen, San Diego, Calif.). This construct is then transfected into COS-7 cells or CHO cells or cell lines and membranes from these cells are analyzed for expression of the BK-2 receptor. Membranes prepared from transfected cells contain specific BK binding sites with a $K_D$ of 0.13+/−0.09 nM as determined by saturation binding analysis (Data not shown). The level of expressed receptor ranges from 210 to 450 fmole/mg protein. Scatchard analysis of the saturation binding data suggests that there are two classes of BK binding sites on the membrane, a high affinity site ($K_D$=0.13 nM) and a lower affinity site that is not well defined by saturation analysis ($K_D$=3 nM–3 uM). The lower affinity sites may arise from BK receptors which are not coupled to G-proteins. Membranes prepared from mock transfected COS-7 cells did not contain any detectable BK specific binding sites. This functional expression of a human BK bradykinin receptor is particularly suitable for designing methods of using the protein to screen for antagonists or agonists of this BK receptor site and, therefore, is critical for drug discovery in this important area.

Competition binding studies indicate that the cloned BK receptor binds BK analogues with the specificity of BK>lys-BK>met-lys-BK (Data not shown). In contrast, peptides reported to be specific for the BK-1 receptor have a very low affinity for this cloned receptor. At a concentration of 10 uM, the BK-1 agonist Des-Arg $^9$BK and the BK antagonist Des-Arg$^9$, LeuBK inhibit BK binding by 18% and 11% respectively. No competition for BK binding is seen with the peptides angiotensin I and II, neurotensin, oxytocin, and endothelin. These results indicate that the receptor cloned and described in the instant application has the pharmacological properties expected for a BK-2 bradykinin receptor.

To further illustrate this principle, the ability of the human BK-2 receptor to interact with well known selective BK-2 antagonists is analyzed (Data not shown). Competition binding studies indicate that Hoe 140 (Hock et al., Br. J. Pharmacol. 102, 774–777 (1991)), D-Arg$^0$-[Hyp$^3$,Thi$^5$,D-Tic$^7$,Oic$^8$]BK is a potent inhibitor with an IC$_{50}$ for the cloned human receptor of 65 pM. This value is in sharp contrast to the IC$_{50}$ of Hoe 140 previously reported from binding studies on guinea pig ileum membranes of 1.07 nM. See Hock et al. The higher affinity for Hoe 140 observed with the cloned human receptor of the instant invention may arise from structural differences between the human and guinea pig BK-2 receptors, from heterogeneity of guinea pig ileum BK-2 receptors, or from differences in experimental design. [$^3$H]BK binding to the human BK-2 receptor of this invention may also be displaced by the known BK-2 antagonists D-Arg$^0$-[Hyp$^{2,3}$,-Thi$^{5,8}$D-Phe$^7$]BK, (IC$_{50}$=27 nM) and [Thi$^{5,8}$,D-Phe$^7$]BK, (IC$_{50}$=180 nM).

In order to simplify the following Examples and the Detailed Description, certain terms will be defined.

Fibroblasts are spindle shaped cells generally responsible for formation of extracellular fibers such as collagen. In this specification, a cDNA library was prepared from human CCD-16Lu fibroblast cells.

PCR is the polymerase chain reaction—a technique for copying the complementary strands of a target DNA molecule simaltaneously for a series of cycles until the desired amount is obtained. First, primers are synthesized that have nucleotide sequences complementary to the DNA that flanks the target region. The DNA is heated to separate the complementary strands and then cooled to let the primers bind to the flanking sequences. A heat-stable DNA polymerase is added, and the reaction is allowed to proceed for a series of replication cycles. Twenty will yield a millionfold amplification; thirty cycles will yield an amplification factor of one billion. See Appendix C, 1985, Saiki, Mullis et al.: Taq DNA polymerase.

Transfection is the incorporation by a cell of foreign DNA into cultured eucaryotic cells (such as COS cells) by exposing them to this DNA.

COS cells are a monkey cell line that has been transformed by an SV40 viral genome containing a defective origin of viral replication. When introduced into COS cells, recombinant RNAs or DNAs containing the SV40 origin and a foreign gene (such as BK-2 cDNA) replicate many copies.

SV40 is a DNA virus that readily infects cultured primate cells. SV40 replicates in the nuclei of host cells and becomes stably integrated into the host genome.

Plasmids are designated by a low case p preceded or followed by capital letters and/or numbers. The starting plasmids used in this invention are commercially available, are publicly available on an unrestricted basis, or can be constructed from such available plasmids in accordance with known procedures. In addition, other equivalent plasmids or constructs will be readily apparent to one skilled in the art. Vectors generally comprise plasmids, viruses (including phage), and integratable DNA fragments (i.e., fragments integratable into the host genome by recombination). Vectors may replicate and function independently of the host genome or may integrate into the host genome. Vectors are essentially replicable DNA constructs. Plasmids are the most commonly used form of vector. However, all other forms of vectors which serve an equivalent function of carrying or transporting a cDNA coding for a bradykinin BK-2 receptor are suitable for use herein.

An expression vector is a replicable DNA construct in which a DNA sequence encoding a BK-2 bradykinin receptor is operably linked to suitable control sequences capable of effecting the expression of BK-2 bradykinin receptor in a suitable host. Control sequences include a transcriptional promoter, an optional operator sequence to control trascription, a sequence encoding suitable mRNA binding sites, and sequences which control the termination of transcription and translation. Certain vectors, such as amplification vectors, do not need expression control domains but rather need the ability to replicate in a host, usually conferred by an origin of replication, and a selection gene to facilitate recognition of transformants.

Transformed host cells are cells which have been transformed or transfected with bradykinin BK-2 vectors constructed using recombinant DNA techniques. Expressed BK-2 bradykinin receptor will be deposited in the cell membrane of the host cell. Transformed cells may also be used for cloning or amplifying bradykinin BK-2 DNA.

Expression vectors normally contain a promoter which is recognized by the host cell. Viral sources often provide the transcriptional and translational control sequences necessary to transform vertebrate cells. Simian Virus 40 (SV40) is often used. As indicated earlier, COS cells contain a defective SV40 origin of replication and are subsequently transfected with an expression construct containing a bradykinin BK-2 cDNA and an active SV40 origin of replication. Alternatively, the host cell may provide an origin of replication if it is integrated into the host cell chromosome.

Cultures of cells derived from multicellular organisms are the preferred hosts for bradykinin BK-2 synthesis. Mammalian cells are the most preferred. Propagation of such cells in cell culture is known. See Kruse and Patterson, Ed. *Tissue Culture*, Academic Press (1973). Various mammalian cell lines include VERO and HeLa cells, Chinese hamster ovary (CHO) cell lines, and WI138, BHK, COS-7, CV and MDCK cell lines. Preferrably, COS-7 cells or CHO cells are used in the instant invention. Expression vectors for these cells normally include an origin of replication, a promoter located upstream from the gene to be expressed, along with a ribosome binding site, RNA splice site (if intron-containing genomic DNA is used), a polyadenylation site, and a transcriptional termination sequence.

A transgenic mouse carrying the human BK-2 receptor gene may be generated by direct replacement of the mouse BK-2 receptor gene with the human BK-2 receptor gene by homologous recombination. The transgenic mouse carrying the human BK-2 gene will be useful in characterizing the in vivo efficacy of antagonists of the human BK-2 gene isolated from in vitro studies.

Compositions claimed in the instant invention may be prepared according to methods known in the art. For example, BK-2 bradykinin receptor protein may be mixed with pharmaceutically acceptable carriers. These carriers will be non-toxic to recipients or patients in need thereof at the dosages and concentrations employed. Ordinarily, the preparation of such compositions entails combining the BK receptor protein with buffers, antioxidants such as ascorbic acid, low molecular weight polypeptides, proteins, amino acids, carbohydrate including glucose or dextrins, chelating agents such as EDTA, glutathione and other stabilizers and excipients. BK receptors may be administered to counteract the effects of excess bradykinin or to absorb autoimmune anti-bradykinin BK-2 receptor antibody.

EXAMPLE 1

Preparation of the cDNA Probe by PCR

Reverse PCR with *Thermus thermophilus* DNA polymerase (Perkin Elmer Cetus) was performed using human uterine mRNA (Clonetech). Annealing of the reverse primer and reverse transcription was done by incubating the PCR reaction minus the forward primer for 10 minutes each at room temperature, 42° C., and 60° C. PCR was performed for 35 cycles of 1 minute each at 94°, 40°, and 60° C. Two rounds of PCR were performed using degenerate primers with the restriction site adapters, NotI on the forward primer CGGCGGCCGCGCNAAYAAYTTYGAYTGG (SEQ ID NO: 10) and XhoI on the reverse primer CGCTC-GAGCGYTTYTTYTTYTCNGTYTG (SEQ ID NO: 11) The degenerate primers were designed using the hypothesized rat amino acid sequence of the rat BK-2 bradykinin receptor. These primers were removed using a CENTRO-CON 30 (AMICON, Beverly, Mass.) and a third round of PCR was performed using a second pair of nested primers (with restriction site adapters) GCGCGGCCGCAAYAC-NATGATHTA (SEQ ID NO: 12) and CGCTCGAGACYT-CYTTRAAYTTYTTCAT (SEQ ID NO: 13). PCR products were then analyzed on a 3.5% NUSIEVE (FMC BIOPRODUCTS, Rockland, Me.) gel. A 386 bp PCR product (Seq. ID No. 7) was then subcloned into pBLUESCRIPT (STRATGENE, La Jolla, Calif.) and characterized by DNA sequence analysis. The probe utilized for screening was prepared by random primed synthesis (Boehringer Mannheim Biochemicals) in the presence of $[alpha-^{32}P]dCTP$ (400 Ci/mmole).

EXAMPLE 2

Isolation of cDNA

Isolation of cDNA coding for the human BK-2 bradykinin receptor was accomplished by first, isolating mRNA from the human cell line CCD-16Lu (CCL 204 obtained from the ATCC, Rockville, Md.) using the INVITROGEN FAST TRACK system. According to this procedure, CCD-16Lu cells were harvested in lysis buffer (Invitrogen, San Diego, Calif.). The lysate was homogenized in a sterile Dounce homogenizer. The lysate was incubated at 45° C. for 1 hour and then spun at 4000×g to remove insoluble material. The NaCl concentration was adjusted to 0.5M NaCl and a Oligo (dT) tablet was added, this mixture was then incubated by gentle rocking at room temperature for 1 hour. The Oligo (dT) was then pelleted at 4000×g. The pellet was washed several times with binding buffer (Invitrogen, San Diego, Calif.) and then placed into a spin-column/microcentirfuge set (Invitrogen, San Diego, Calif.). The mRNA was eluted from the column with elution buffer (Invitrogen, San Diego, Calif.) and precipitated with sodium acetate and ethanol. cDNA was then prepared from mRNA using the BRL cDNA Synthesis System (BRL, Gaithersburg, Md.). See Gubler et al., Gene, 25, 263 (1983) as modified by BRL. BstXI adapters were then added and the modified cDNA ligated into pcDNA II (INVITROGEN). Bacterial colonies were then plated at a density of 30,000 colonies per plate and transferred to duplicate Durulose-UV (STRATAGENE) filters using standard techniques (MANIATIS). The probe utilized for screening was generated by random primed synthesis as described above. Duplicate filters were also hybridized with $1.5 \times 10^6$ cpm/ml [$^{32}$P] labeled probe in 50% formamide hybridization solution, [5×SSC, 5×Denhart's, 100 ug/ml DNA, (SIGMA, St Louis, Mo.)] at 50° C. for 12 hours. The filters were washed at high stringency in a final wash of 0.1×SSC, 0.1% SDS at 60° C. Positive colonies were then rescreened as before. Plasmid was then isolated from second round positives and the DNA sequence was determined by double strand DNA sequencing using the SANGER METHOD and SEQUENASE (US BIOCHEMICALS, Cleveland, Ohio).

EXAMPLE 3
Transfection and Membrane Preparation

In order to enable expression of the cDNA that encodes for the BK-2 bradykinin receptor, COS-7 cells were transfected using LIPOFECTIN (BRL, Gaithersburg, Md.) with 50 ug/$10^7$ cells of the BK-2 receptor cDNA subcloned into the eukaryotic expression vector pcDNA I-Neo (Invitrogen). Cells were then harvested after 72 hours and the membranes containing the expressed receptor protein were prepared by scraping the cells in phosphate buffered saline solution and centrifuging for ten minutes at 500×g. The cell pellet was then resuspended and homogenized with a Polytron in 20 mM N-tris(hydroxymethyl)methyl-2-aminoethane sulfonic acid (TES, pH 6.8 at room temperature) buffer containing 1 mM 1,10 phenanthroline. The homogenate was then centrifuged for ten minutes at 500×g. The final membrane pellet was resuspended in assay buffer (TES plus 0.1% protease free bovine serum albumin, 5 uM MK-422 (enalaprilat; Gross et al., 1981) and 140 ug/ml bacitracin using a motor-driven teflon-glass tissue homogenizer. Protein determination was performed by the method of Bradford using bovine IgG as the standard. See Bradford, M. A. Anal. Biochem. 72, 248–254 (1976).

EXAMPLE 4
Binding Assays

Binding assays were then performed to determine receptor antagonist or agonist interaction. The assays utilized in the instant invention follow the method of Manning et al., *J. Pharmacol. Exp. Ther.*, 237, 504–512 (1986). [$^3$H]BK at various concentrations was incubated for 60 minutes at 25° C. with approximately 50 ug membrane protein from COS-7 cells in a volume of 1 ml. The assay was terminated by filtration over Whatman GF/B filters presoaked for 3 hours in 0.1% polyethyleneimine using a BRANDEL M-24 CELL HARVESTER (BRANDEL, Gaithersburg, Md.). The tubes were rinsed two times with 4 ml ice-cold 10 uM TEX and the filter bound radioactivity was quantitated by liquid scintillation counting. Nonspecific binding was determined by performing incubation in the presence of 1 uM BK and generally represents less than 5% of the total binding at 100 pM [$^3$H]BK. Competition binding experiments, in the presence of 100 pM[$^3$H]BK, were performed with varying concentrations of the test compound(s). The competition and saturation experiments were analyzed using the EBDA program of McPherson. See McPherson, G. A. *J Pharmacol. Methods* 14, 213–218 (1985).

BK-Induced Cystosolic $Ca^{2+}$ Increases in Chinese Hamster Ovary Cells

Preconfluent CHO cells were lifted from polystyrene culture flasks using phosphate-buffered slaine containing 2 mM EDTA. The cells were washed twice by centrifugation and resuspended at a density of $2 \times 10^6$ cells/ml in a physiolocical solution buffered with 10 mM HEPES, pH 7.4. The cells wee incubated with 1 uM fura-2 for 40 minutes at 37° C., washed twice by centrifugation with fresh buffer and resuspended again to $2 \times 10^6$ cells/ml. Two ml aliquots of the suspension were then added to glass cuvettes and placed in the thermostatically controlled (37° C.) holder of a DEL-TASCAN (Photon Technology International) dual wavelength fluroimeter. Excitation was performed at 340 nm and 380 nm and emission was monitered at 510 nm. After two minutes, agonist (bradykinin or test compound) was added and the 340/380 excitation ratio was read for an additional 2 minutes. When used, antagonists were added 15 seconds prior to agonist.

Functional expression of the human BK-2 receptor was obtained by placing the entire BK-2 clone under the control of the CMV promoter (Human cytomegalo virus) in the eukaryotic expression vector, pCDNAI-Neo (Invitrogen, San Diego, Calif.). This construct was then transfected into COS-7 cells or CHO cells or cell lines and membranes from these cells were analyzed for expression of the BK-2 receptor as indicated above. Membranes prepared from transfected cells contain specific BK binding sites with a $K_D$ of 0.13+/−0.09 nM as determined by saturation binding analysis (Data not shown). The level of expressed receptor ranges from 210 to 450 fmole/mg protein. Scatchard analysis of the saturation binding data suggested that there are two classes of BK binding sites on the membrane, a high affinity site ($K_D$=0.13 nM) and a lower affinity site that is not well defined by saturation analysis ($K_D$=3 nM–3 uM). The lower affinity sites may arise from BK receptors which are not coupled to G-proteins. Membranes prepared from mock transfected COS-7 cells did not contain any detectable BK specific binding sites.

Competition binding studies in the COS-7 expressed receptor indicated that the cloned BK receptor binds BK analogues with the specificity of BK>lys-BK>met-lys-BK (Data not shown). In contrast, peptides reported to be specific for the BK-1 receptor have a very low affinity for this cloned receptor. At a concentration of 10 uM, the BK-1 agonist Des-Arg$^9$BK and the BK antagonist Des-Arg$^9$, LeuBK inhibited BK binding by 18% and 11% respectively. No competition for BK binding was seen with the peptides angiotensin I and II, neurotensin, oxytocin, and endothelin. These results indicated that the receptor cloned and described in the instant application has the pharmacological properties expected for a BK-2 bradykinin receptor.

To further illustrate this principle, the ability of the human BK-2 receptor to interact with well known selective BK-2 antagonists was analyzed (Data not shown). Competition binding studies indicated that Hoe 140 (Hock et al., Br. J. Pharmacol. 102, 774–777 (1991)), D-Arg$^0$-[Hyp$^3$, Thi$^5$,D-Tic$^7$,Oic$^8$]BK was a potent inhibitor with an IC$_{50}$ for the cloned human receptor of 65 pM. [$^3$H]BK binding to the human BK-2 receptor of this invention was displaced by the known BK-2 antagonists D-Arg$^0$-Hyp$^{2,3}$,Thi$^{5,8}$D-Phe$^7$BK, (IC$_{50}$=27 nM) and [Thi$^{5,8}$,D-Phe$^7$]BK, (IC$_{50}$=180 nM).

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 1:

Arg Pro Pro Gly Phe Ser Pro Phe Arg
1               5

(2) INFORMATION FOR SEQ ID NO: 2:

(i) SEQUENCE CHARACTERISTICS:
      (A) LENGTH: 364 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 2:

Met Leu Asn Val Thr Leu Gln Gly Pro Thr Leu Asn Gly Thr Phe Ala
1               5                   10                  15

Gln Ser Lys Cys Pro Gln Val Glu Trp Leu Gly Trp Leu Asn Thr Ile
                20                  25                  30

Gln Pro Pro Phe Leu Trp Val Leu Phe Leu Ala Thr Leu Glu Asn
            35                  40                  45

Ile Phe Val Leu Ser Val Phe Cys Leu His Lys Ser Ser Cys Thr Val
        50                  55                  60

Ala Glu Ile Tyr Leu Gly Asn Leu Ala Ala Ala Asp Leu Ile Leu Ala
65                  70                  75                  80

Cys Gly Leu Pro Phe Trp Ala Ile Thr Ile Ser Asn Asn Phe Asp Trp
                85                  90                  95

Leu Phe Gly Glu Thr Leu Cys Arg Val Val Asn Ala Ile Ile Ser Met
                100                 105                 110

Asn Leu Tyr Ser Ser Ile Cys Phe Leu Met Leu Val Ser Ile Asp Arg
            115                 120                 125

Tyr Leu Ala Leu Val Lys Thr Met Ser Met Gly Arg Met Arg Gly Val
            130                 135                 140

Arg Trp Ala Lys Leu Tyr Ser Leu Val Ile Trp Gly Cys Thr Leu Leu
145                 150                 155                 160

Leu Ser Ser Pro Met Leu Val Phe Arg Thr Met Lys Glu Tyr Ser Asp
                165                 170                 175

Glu Gly His Asn Val Thr Ala Cys Val Ile Ser Tyr Pro Ser Leu Ile
            180                 185                 190

Trp Glu Val Phe Thr Asn Met Leu Leu Asn Val Val Gly Phe Leu Leu
            195                 200                 205

Pro Leu Ser Val Ile Thr Phe Cys Thr Met Gln Ile Met Gln Val Leu
        210                 215                 220

Arg Asn Asn Glu Met Gln Lys Phe Lys Glu Ile Gln Thr Glu Arg Arg

```
225                 230                 235                 240
Ala Thr Val Leu Val Leu Val Leu Leu Leu Phe Ile Ile Cys Trp
                245                 250                 255
Leu Pro Phe Gln Ile Ser Thr Phe Leu Asp Thr Leu His Arg Leu Gly
                260                 265                 270
Ile Leu Ser Ser Cys Gln Asp Glu Arg Ile Ile Asp Val Ile Thr Gln
                275                 280                 285
Ile Ala Ser Phe Met Ala Tyr Ser Asn Ser Cys Leu Asn Pro Leu Val
                290                 295                 300
Tyr Val Ile Val Gly Lys Arg Phe Arg Lys Lys Ser Trp Glu Val Tyr
305                 310                 315                 320
Gln Gly Val Cys Gln Lys Gly Gly Cys Arg Ser Glu Pro Ile Gln Met
                325                 330                 335
Glu Asn Ser Met Gly Thr Leu Arg Thr Ser Ile Ser Val Glu Arg Gln
                340                 345                 350
Ile His Lys Leu Gln Asp Trp Ala Gly Ser Arg Gln
                355                 360
```

(2) INFORMATION FOR SEQ ID NO: 3:

(i) SEQUENCE CHARACTERISTICS:
        (A) LENGTH: 1179 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

```
GTCCAAATGT TCTCTCCCTG GAAGATATCA ATGTTTCTGT CTGTTCGTGA G GACTCCGTG       60
CCCACCACGG CCTCTTTCAG CGCCGACATG CTCAATGTCA CCTTGCAAGG G CCCACTCTT     120
AACGGGACCT TTGCCCAGAG CAAATGCCCC CAAGTGGAGT GGCTGGGCTG G CTCAACACC     180
ATCCAGCCCC CCTTCCTCTG GGTGCTGTTC GTGCTGGCCA CCCTAGAGAA C ATCTTTGTC     240
CTCAGCGTCT TCTGCCTGCA CAAGAGCAGC TGCACGGTGG CAGAGATCTA C CTGGGGAAC     300
CTGGCCGCAG CAGACCTGAT CCTGGCCTGC GGGCTGCCCT TCTGGGCCAT C ACCATCTCC     360
AACAACTTCG ACTGGCTCTT TGGGGAGACG CTCTGCCGCG TGGTGAATGC C ATTATCTCC     420
ATGAACCTGT ACAGCAGCAT CTGTTTCCTG ATGCTGGTGA GCATCGACCG C TACCTGGCC     480
CTGGTGAAAA CCATGTCCAT GGGCCGGATG CGCGGCGTGC GCTGGGCCAA G CTCTACAGC     540
TTGGTGATCT GGGGGTGTAC GCTGCTCCTG AGCTCACCCA TGCTGGTGTT C GGACCATG     600
AAGGAGTACA GCGATGAGGG CCACAACGTC ACCGCTTGTG TCATCAGCTA C CCATCCCTC     660
ATCTGGGAAG TGTTCACCAA CATGCTCCTG AATGTCGTGG GCTTCCTGCT G CCCCTGAGT     720
GTCATCACCT TCTGCACGAT GCAGATCATG CAGGTGCTGC GGAACAACGA G ATGCAGAAG     780
TTCAAGGAGA TCCAGACGGA GAGGAGGGCC ACGGTGCTAG TCCTGGTTGT G CTGCTGCTA     840
TTCATCATCT GCTGGCTGCC CTTCCAGATC AGCACCTTCC TGGATACGCT G CATCGCCTC     900
GGCATCCTCT CCAGCTGCCA GGACGAGCGC ATCATCGATG TAATCACACA G ATCGCCTCC     960
TTCATGGCCT ACAGCAACAG CTGCCTCAAC CCACTGGTGT ACGTGATCGT G GGCAAGCGC    1020
TTCCGAAAGA AGTCTTGGGA GGTGTACCAG GGAGTGTGCC AGAAGGGGG C TGCAGGTCA    1080
GAACCCATTC AGATGGAGAA CTCCATGGGC ACACTGCGGA CCTCCATCTC C GTGGAACGC    1140
CAGATTCACA AACTGCAGGA CTGGGCAGGG AGCAGACAG                          1179
```

(2) INFORMATION FOR SEQ ID NO: 4:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

```
CTCCGAGGAG GGGTGGGGAC GGTCCTGACG GTGGGGACAT CAGGCTGCCC C GCAGTACCA        60

GGGAGCGACT TGAAGTGCCC ATGCCGCTTG CTCCGGGAGA AGCCCAGGTG T GGCCTCACT       120

CACATCCCAC TCTGA                                                        135
```

(2) INFORMATION FOR SEQ ID NO: 5:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

```
TGAGCAAACG CCAGCAGGGC TGCTGTGAAT TTGTGTAAGG ATTGAGGGAC A GTTGCTTTT        60

CAGG                                                                     64
```

(2) INFORMATION FOR SEQ ID NO: 6:

(i) SEQUENCE CHARACTERISTICS:
        (A) LENGTH: 1378 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO: 6:

```
CTCCGAGGAG GGGTGGGGAC GGTCCTGACG GTGGGGACAT CAGGCTGCCC C GCAGTACCA        60

GGGAGCGACT TGAAGTGCCC ATGCCGCTTG CTCCGGGAGA AGCCCAGGTG T GGCCTCACT       120

CACATCCCAC TCTGAGTCCA AATGTTCTCT CCCTGGAAGA TATCAATGTT T CTGTCTGTT       180

CGTGAGGACT CCGTGCCCAC CACGGCCTCT TTCAGCGCCG ACATGCTCAA T GTCACCTTG       240

CAAGGGCCCA CTCTTAACGG GACCTTTGCC CAGAGCAAAT GCCCCAAGT  G GAGTGGCTG       300

GGCTGGCTCA ACACCATCCA GCCCCCCTTC CTCTGGGTGC TGTTCGTGCT G GCCACCCTA       360

GAGAACATCT TTGTCCTCAG CGTCTTCTGC CTGCACAAGA GCAGCTGCAC G GTGGCAGAG       420

ATCTACCTGG GAACCTGGC  CGCAGCAGAC CTGATCCTGG CCTGCGGGCT G CCCTTCTGG       480

GCCATCACCA TCTCCAACAA CTTCGACTGG CTCTTTGGGG AGACGCTCTG C CGCGTGGTG       540

AATGCCATTA TCTCCATGAA CCTGTACAGC AGCATCTGTT TCCTGATGCT G GTGAGCATC       600

GACCGCTACC TGGCCCTGGT GAAAACCATG TCCATGGGCC GGATGCGCGG C GTGCGCTGG       660

GCCAAGCTCT ACAGCTTGGT GATCTGGGGG TGTACGCTGC TCCTGAGCTC A CCCATGCTG       720

GTGTTCCGGA CCATGAAGGA GTACAGCGAT GAGGGCCACA ACGTCACCGC T TGTGTCATC       780

AGCTACCCAT CCCTCATCTG GGAAGTGTTC ACCAACATGC TCCTGAATGT C GTGGGCTTC       840

CTGCTGCCCC TGAGTGTCAT CACCTTCTGC ACGATGCAGA TCATGCAGGT G CTGCGGAAC       900
```

```
AACGAGATGC AGAAGTTCAA GGAGATCCAG ACGGAGAGGA GGGCCACGGT G CTAGTCCTG      960

GTTGTGCTGC TGCTATTCAT CATCTGCTGG CTGCCCTTCC AGATCAGCAC C TTCCTGGAT     1020

ACGCTGCATC GCCTCGGCAT CCTCTCCAGC TGCCAGGACG AGCGCATCAT C GATGTAATC     1080

ACACAGATCG CCTCCTTCAT GGCCTACAGC AACAGCTGCC TCAACCCACT G GTGTACGTG     1140

ATCGTGGGCA AGCGCTTCCG AAAGAAGTCT TGGGAGGTGT ACCAGGGAGT G TGCCAGAAA     1200

GGGGGCTGCA GGTCAGAACC CATTCAGATG GAGAACTCCA TGGGCACACT G CGGACCTCC     1260

ATCTCCGTGG AACGCCAGAT TCACAAACTG CAGGACTGGG CAGGGAGCAG A CAGTGAGCA     1320

AACGCCAGCA GGGCTGCTGT GAATTTGTGT AAGGATTGAG GGACAGTTGC T TTTCAGG       1378

(2) INFORMATION FOR SEQ ID NO: 7:

(i) SEQUENCE CHARACTERISTICS:
        (A) LENGTH: 387 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO: 7:

AATGCCATTA TCTCCATGAA CCTGTACAGC AGCATCTGTT TCCTGATGCT G GTGAGCATC       60

GACCGCTACC TGGCCCTGGT GAAAACCATG TCCATGGGCC GGATGCGCGG C GTGCGCTGG      120

GCCAAGCTCT ACAGCTTGGT GATCTGGGGG TGTACGCTGC TCCTGAGCTC A CCCATGCTG      180

GTGTTCCGGA CCATGAAGGA GTACAGCGAT GAGGGCCACA ACGTCACCGC T TGTGTCATC      240

AGCTACCCAT CCCTCATCTG GAAGTGTTC ACCAACATGC TCCTGAATGT C GTGGGCTTC       300

CTGCTGCCCC TGAGTGTCAT CACCTTCTGC ACGATGCAGA TCATGCAGGT G CTGCGGAAC      360

AACGAGATGC AGAAGTTCAA GGAGATC                                           387

(2) INFORMATION FOR SEQ ID NO: 8:

(i) SEQUENCE CHARACTERISTICS:
        (A) LENGTH: 775 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO: 8:

CCTCCGAGGA GGGGTGGGGA CGGTCCTGAC GGTGGGGACA TCAGGCTGCC C CGCAGTACC       60

AGGGAGCGAC TTGAAGTGCC CATGCCGCTT GCTCCGGGAG AAGCCCAGGT G TGGCCTCAC      120

TCACATCCCA CTCTGAGTCC AAATGTTCTC TCCCTGGAAG ATATCAATGT T TCTGTCTGT      180

TCGTGAGGAC TCCGTGCCCA CCACGGCCTC TTTCAGCGCC GACATGCTCA A TGTCACCTT      240

GCAAGGGCCC ACTCTTAACG GGACCTTTGC CCAGAGCAAA TGCCCCAAG T GGAGTGGCT       300

GGGCTGGCTC AACACCATCC AGCCCCCCTT CCTCTGGGTG CTGTTCGTGC T GGCCACCCT      360

AGAGAACATC TTTGTCCTCA GCGTCTTCTG CCTGCACAAG AGCAGCTGCA C GGTGGCAGA      420

GATCTACCTG GGAACCTGG CCGCAGCAGA CCTGATCCTG GCCTGCGGGC T GCCCTTCTG       480

GGCCATCACC ATCTCCAACA ACTTCGACTG GCTCTTTGGG GAGACGCTCT G CCGCGTGGT      540

GAATGCCATT ATCTCCATGA ACCTGTACAG CAGCATCTGT TTCCTGATGC T GGTGAGCAT      600

CGACCGCTAC CTGGCCCTGG TGAAAACCAT GTCCATGGGC CGGATGCGCG G CGTGCGCTG      660

GGCCAAGCTC TACAGCTTGG TGATCTGGGG GTGTACGCTG CTCCTGAGCT C ACCCATGCT      720
```

```
GGTGTTCCGG ACCATGAAGG AGTACAGCGA TGAGGGCCAC AACGTCACCG C TTGT         775
```

(2) INFORMATION FOR SEQ ID NO: 9:

(i) SEQUENCE CHARACTERISTICS:
        (A) LENGTH: 909 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO: 9:

```
TGCCCTTCTG GGCCATCACC ATCTCCAACA ACTTCGACTG GCTCTTTGGG G AGACGCTCT     60
GCCGCGTGGT GAATGCCATT ATCTCCATGA ACCTGTACAG CAGCATCTGT T TCCTGATGC    120
TGGTGAGCAT CGACCGCTAC CTGGCCCTGG TGAAAACCAT GTCCATGGGC C GGATGCGCG    180
GCGTGCGCTG GGCCAAGCTC TACAGCTTGG TGATCTGGGG GTGTACGCTG C TCCTGAGCT    240
CACCCATGCT GGTGTTCCGG ACCATGAAGG AGTACAGCGA TGAGGGCCAC A ACGTCACCG    300
CTTGTGTCAT CAGCTACCCA TCCCTCATCT GGGAAGTGTT CACCAACATG C TCCTGAATG    360
TCGTGGGCTT CCTGCTGCCC CTGAGTGTCA TCACCTTCTG CACGATGCAG A TCATGCAGG    420
TGCTGCGGAA CAACGAGATG CAGAAGTTCA AGGAGATCCA GACGGAGAGG A GGGCCACGG    480
TGCTAGTCCT GGTTGTGCTG CTGCTATTCA TCATCTGCTG GCTGCCCTTC C AGATCAGCA    540
CCTTCCTGGA TACGCTGCAT CGCCTCGGCA TCCTCTCCAG CTGCCAGGAC G AGCGCATCA    600
TCGATGTAAT CACACAGATC GCCTCCTTCA TGGCCTACAG CAACAGCTGC C TCAACCCAC    660
TGGTGTACGT GATCGTGGGC AAGCGCTTCC GAAAGAAGTC TTGGGAGGTG T ACCAGGGAG    720
TGTGCCAGAA AGGGGCTGC AGGTCAGAAC CCATTCAGAT GGAGAACTCC A TGGGCACAC    780
TGCGGACCTC CATCTCCGTG AACGCCAGA TTCACAAACT GCAGGACTGG G CAGGGAGCA    840
GACAGTGAGC AAACGCCAGC AGGGCTGCTG TGAATTTGTG TAAGGATTGA G GGACAGTTG    900
CTTTTCAGG                                                              909
```

(2) INFORMATION FOR SEQ ID NO: 10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

```
CGGCGGCCGC GCNAAYAAYT TYGAYTGG                                          28
```

(2) INFORMATION FOR SEQ ID NO: 11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

```
CGCTCGAGCG GYTTYTTYTT YTCNGTYTG                                         29
```

-continued (2) INFORMATION FOR SEQ ID NO: 12:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 12:

GCGCGGCCGC AAYACNATGA THTA        24

(2) INFORMATION FOR SEQ ID NO: 13:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 13:

CGCTCGAGAC YTCYTTRAAY TTYTTCAT        28

What is claimed is:

1. A human bradykinin BK-2 receptor protein comprising the amino acid sequence: (SEQ. ID NO: 2)

```
Met Leu Asn Val Thr Leu Gln Gly Pro Thr Leu Asn
1               5                       10
Gly Thr Phe Ala Gln Ser Lys Cys Pro Gln Val Glu
            15                  20
Trp Leu Gly Trp Leu Asn Thr Ile Gln Pro Pro Phe
25                      30                  35
Leu Trp Val Leu Phe Val Leu Ala Thr Leu Glu Asn
                40                  45
Ile Phe Val Leu Ser Val Phe Cys Leu His Lys Ser
        50                  55                  60
Ser Cys Thr Val Ala Glu Ile Tyr Leu Gly Asn Leu
                65                      70
Ala Ala Ala Asp Leu Ile Leu Ala Cys Gly Leu Pro
            75                      80
Phe Trp Ala Ile Thr Ile Ser Asn Asn Phe Asp Trp
85                      90                      95
Leu Phe Gly Glu Thr Leu Cys Arg Val Val Asn Ala
                100                     105
Ile Ile Ser Met Asn Leu Tyr Ser Ser Ile Cys Phe
        110                     115                     120
Leu Met Leu Val Ser Ile Asp Arg Tyr Leu Ala Leu
                    125                     130
Val Lys Thr Met Ser Met Gly Arg Met Arg Gly Val
                135                     140
Arg Trp Ala Lys Leu Tyr Ser Leu Val Ile Trp Gly
145                     150                     155
Cys Thr Leu Leu Leu Ser Ser Pro Met Leu Val Phe
                    160                     165
Arg Thr Met Lys Glu Tyr Ser Asp Glu Gly His Asn
                170                     175                     180
Val Thr Ala Cys Val Ile Ser Tyr Pro Ser Leu Ile
                    185                     190
Trp Glu Val Phe Thr Asn Met Leu Leu Asn Val Val
                195                     200
Gly Phe Leu Leu Pro Leu Ser Val Ile Thr Phe Cys
205                     210                     215
Thr Met Gln Ile Met Gln Val Leu Arg Asn Asn Glu
                220                     225
Met Gln Lys Phe Lys Glu Ile Gln Thr Glu Arg Arg
        230                     235                     240
Ala Thr Val Leu Val Leu Val Val Leu Leu Leu Phe
                    245                     250
Ile Ile Cys Trp Leu Pro Phe Gln Ile Ser Thr Phe
            255                     260
Leu Asp Thr Leu His Arg Leu Gly Ile Leu Ser Ser
265                     270                     275
Cys Gln Asp Glu Arg Ile Ile Asp Val Ile Thr Gln
                280                     285
Ile Ala Ser Phe Met Ala Tyr Ser Asn Ser Cys Leu
        290                     295                     300
Asn Pro Leu Val Tyr Val Ile Val Gly Lys Arg Phe
                    305                     310
Arg Lys Lys Ser Trp Glu Val Tyr Gln Gly Val Cys
            315                     320
Gln Lys Gly Gly Cys Arg Ser Glu Pro Ile Gln Met
325                     330                     335
Glu Asn Ser Met Gly Thr Leu Arg Thr Ser Ile Ser
                340                     345
```

-continued

Val Glu Arg Gln Ile His Lys Leu Gln Asp Trp Ala
350                 355                 360
Gly Ser Arg Gln said human bradykinin BK-2 receptor protein being substantially free of other human proteins.

* * * * *